(12) United States Patent
Yao et al.

(10) Patent No.: US 8,097,747 B2
(45) Date of Patent: Jan. 17, 2012

(54) PROCESS FOR THE ALKYLATION OF PHOSPHORUS-CONTAINING COMPOUNDS

(75) Inventors: Qiang Yao, Yorktown Heights, NY (US); Sergi V. Levchik, Croton-on-Hudson, NY (US)

(73) Assignee: ICL-IP America Inc, Ardsley, NY (US)

( * ) Notice: Subject to any disclaimer, the term of this patent is extended or adjusted under 35 U.S.C. 154(b) by 723 days.

(21) Appl. No.: 11/587,220

(22) PCT Filed: Apr. 22, 2005

(86) PCT No.: PCT/US2005/013756
§ 371 (c)(1),
(2), (4) Date: Oct. 6, 2008

(87) PCT Pub. No.: WO2005/105818
PCT Pub. Date: Nov. 10, 2005

(65) Prior Publication Data
US 2009/0054675 A1 Feb. 26, 2009

Related U.S. Application Data

(60) Provisional application No. 60/564,801, filed on Apr. 23, 2004.

(51) Int. Cl.
C07F 9/02 (2006.01)
(52) U.S. Cl. .......................................... 558/87
(58) Field of Classification Search ...................... 558/87
See application file for complete search history.

(56) References Cited

U.S. PATENT DOCUMENTS

| | | | |
|---|---|---|---|
| 2,724,718 A | 11/1955 | Stiles at al. | |
| 4,590,014 A | 5/1986 | Wolf et al. | |
| 4,632,741 A | 12/1986 | Wolf et al. | |
| 6,300,516 B1 | 10/2001 | Weferling et al. | |
| 6,534,673 B1 | 3/2003 | Weferling et al. | |

FOREIGN PATENT DOCUMENTS

| | | |
|---|---|---|
| JP | 5247068 A | 9/1993 |
| JP | 8073720 A1 | 3/1995 |

OTHER PUBLICATIONS

Boyd et al., Tetrahedron Letters, 1994, 35(24):4223-4226.*
Devedjiev et al., "On the Interaction Between Hypophosphorus Acid and Alcohols," Phosohorus and Sulfer, 1987, vol. 31, pp. 7-11.
Boyd et al., "Synthesis of Alkyl Phosphinic Acids from Sily Phosphonites and Alkyl Halides," Tetrahedron Letters, vol. 35, No. 24, pp. 4223-4226, 1994.
Chauzov, et al. "Alkylation of Hydrophosphoryl Compounds by Alcohols. Synthesis of Diorganoalkylphosphine Oxides," Journal of General Chemistry of the USSR, vol. 59, 1989, pp. 2211-2213.
Yamashita et al., "Nucleophilic Substitution with Phosphide Anions Prepared by an Action of Sodium Dihydridobis(2-methoxyethanolato)aluminate on Phosphorus Compounds," Bull Chem. Soc. Japan, vol. 56, 219-222 (1983).
Deprele et al., "Triethyborane-Initiated Room Temperature Radical Addition of Hypophosphites to Olefins: Synthesis of Monosubstituted Phosphinic Acids and Esters," J. Org. Chem. 2001, vol. 66, pp. 6745-6755.
Journal of General Chemistry of the USSR, 1988, vol. 58, Ed. 10, pp. 2398-2399.
Russian Office Action dated Mar. 30, 2009 for related Russian Patent Application No. 2006/141353.
US 6,248,921, 01/2001, Weferling et al. (withdrawn)

* cited by examiner

Primary Examiner — Rei-tsang Shiao
(74) Attorney, Agent, or Firm — Dilworth & Barrese, LLP

(57) ABSTRACT

A process for alkylating a phosphorus-containing compound to provide an alkylated phosphorus-containing compound is provided which comprises alkylating 5 phosphorus-containing compound possessing at least one phosphorus-hydrogen alkylatable site with reactant which generates alkene and/or cycloalkene alkylating agent in situ in the presence of initiator, the alkylene and/or cycloalkylene alkylating agent alkylating the phosphorus-containing component to provide alkylated phosphorus-containing product.

(1)

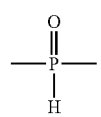

18 Claims, No Drawings

PROCESS FOR THE ALKYLATION OF PHOSPHORUS-CONTAINING COMPOUNDS

CROSS REFERENCE TO RELATED APPLICATION

This invention claims the benefit of U.S. provisional application Ser. No. 60/564,801, filed Apr. 23, 2004, the entire contents of which are incorporated by reference herein.

BACKGROUND OF THE INVENTION

This invention relates to processes for alkylating phosphorus-containing compounds. More particularly, this invention relates to processes for alkylating phosphorus-containing compounds possessing at least one phosphorus-hydrogen

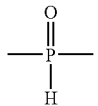

alkylatable site to provide an alkylated phosphorus-containing product, e.g., a mono- or dialkylphosphinic acid or metal salt thereof, an alkylarylphosphinic acid or metal salt thereof, an alkyl alkylphosphonic acid or metal salt thereof, an alkyl or aryl dialkylphosphinate ester, an alkyl or aryl alkylarylphosphinate ester, an alkyl or arylalkylphosphorous acid or metal salt thereof or a dialkyl or diaryl alkylphosphonate ester.

In order to prepare dialkylphosphinic acid derivatives, a complex synthesis route has been used which includes the hydrolysis of methyldichlorophosphine to provide methylphosphinic acid and the subsequent esterification of this acid to provide an alkyl methylphosphinic ester. The second phosphorus-hydrogen bond can also be alkylated in the presence of a free-radical initiator.

The use of dialkylphosphinic acid derivatives as flame retardants for polyesters (poly(ethylene terephthalate) and polybutylene terephthalate)) is described in European Patent Publication No. 699,708. These products are synthesized by a complex process using methyldichlorophosphine which is hydrolyzed to methylphosphinic acid; the ester of this acid has been prepared and isolated as intermediate. To prepare dialkylphosphinic acids or derivatives thereof, alkylphosphinic esters can be alkylated by α-olefins at high temperatures under free-radical catalysis conditions. In the case of the reaction of alkylphosphinic acids under the same conditions, only the disproportionation products, namely, alkylphosphines and alkylphosphonic acids, are obtained while under mild conditions no reaction is observed.

U.S. Pat. No. 4,632,741 describes a process for preparing mixtures of salts of alkylphosphinic and dialkylphosphinic acids by reacting an olefin with a salt of hypophosphorous acid in the presence of a photoinitiator using UV light. U.S. Pat. No. 4,590,014 describes a similar process in which the olefin is reacted with the alkali metal salt of hypophosphorous acid in the presence of a free-radical initiator. However, the predominant product monoalkylphosphinic acid.

U.S. Pat. No. 6,300,516 describes a process for preparing dialkylphosphinic acids and/or alkali metal salts thereof by reacting olefins, particularly ethylene, with alkylphosphinic acid or hypophosphorous acid in the presence of azo free-radical initiator. This process is performed in a pressurized reactor with complicated feeding systems which require special safety features. Only high boiling olefins can be reacted with hypophosphorous acid at atmospheric pressure.

The reaction of hypophosphorous acid with isobutene was reported in the literature (S. Deprele and J-L. Montchamp, J. Org. Chem. 2001, 66, 6745). The reaction was run in the presence of a stoichiometric amount of triethyl borane as initiator. The yield of monosubstituted isobutylphosphinic acid was only 38%.

SUMMARY OF THE INVENTION

It is an object of the invention to provide a process for the alkylation of phosphorous-containing compounds possessing at least one phosphorus-hydrogen

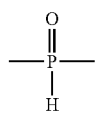

alkylatable site.

It is a particular object of the present invention to provide such a process employing as alkylating agents short chain alkyls which result within a relatively short time in a high yield of the desired alkylated product while avoiding the aforenoted disadvantages associates with the known processes discussed above.

These and other objects of the invention are achieved by the process of alkylation herein which comprises alkylating phosphorous-containing compound possessing at least one phosphorus-hydrogen

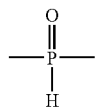

alkylatable site with reactant which generates alkene and/or cycloalkene alkylating agent in situ in the presence of free radical initiator, the alkene and/or cycloalkene alkylating agent alkylating the phosphorus-containing compound to provide alkylated phosphorus-containing product.

Without intending to be bound, it is thought that the reactant which generates alkene or cycloalkene in situ under alkylation conditions produces a sufficient concentration of these compounds that will result in alkylation of the at least one phosphorus-hydrogen alkylatable site present in the starting organophosphorous-containing compound and as the alkenes/cycloalkenes are consumed in the alkylation reaction, the equilibrium shifts towards generation of additional alkenes/cycloalkenes.

DETAILED DESCRIPTION OF THE INVENTION

The phosphorus-containing compound employed as one of the starting reactants herein must contain at least one phosphorus-hydrogen

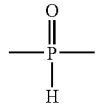

alkylatable site and can contain more than one such site in which case the alkylated phosphorus-containing product may either be partially or fully alkylated.

In one embodiment of the invention, the phosphorus-containing starting reactant is represented by the general formula (I):

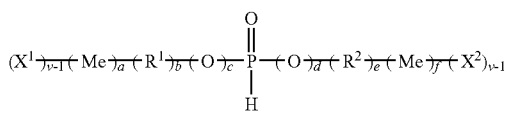

wherein:
$X^1$, where present, is

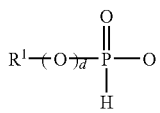

and $X^2$, where present, is

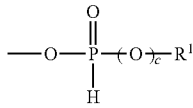

in which $R^1$ is H, alkyl of up to 30 carbon atoms, cycloalkyl of from 3 to 12 carbon atoms or aryl of from 6 to 20 carbon atoms; Me is a metal having a valence v of 1, 2, 3 or 4; $R^2$ is H, alkyl of up to 30 carbon atoms, cycloalkyl of from 3 to 12 carbon atoms or aryl of from 6 to 20 carbon atoms; and, a, b, c, d, e and f each independently is 0 or 1, provided, when a=1, c=1 and b=0, when b=1, a=0 and $x^1$ is not present, when f=1, d=1 and e=0, and when e=1, f=0 and $x^2$ is not present.

Particularly useful phosphorus-containing compounds (I) are those of structural formulas (1)-(6):

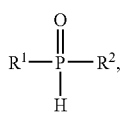   (1)

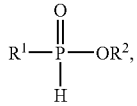   (2)

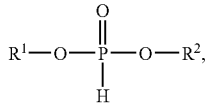   (3)

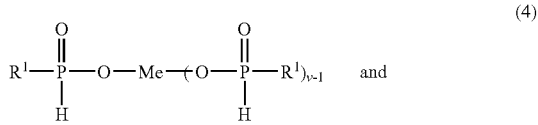   (4)

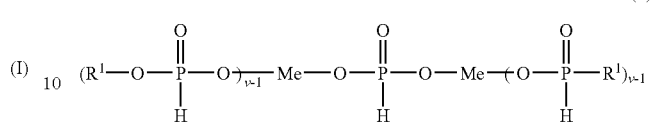   (5)

in which $R^1$, $R^2$, Me and v have the aforestated meanings. In the foregoing structural formulas, $R^1$ is preferably H, $R^2$ is preferably H (except in compounds of structural formula 1 where only $R^1$ may be H) or alkyl of from 1 to 8 carbon atoms and Me is preferably lithium, sodium, potassium, magnesium, calcium, barium, aluminum, titanium, vanadium, chromium, molybdenum, iron, nickel, cobalt, copper or zinc.

Illustrative of the alkylatable phosphorus-containing starting reactants herein are phosphonic acid (phosphorous acid); hypophosphorous acid; phosphinic acid, phosphinous acid; esters of the foregoing such as phosphonic acid tert-butyl ester; phosphonic acid di-tert-butyl ester, phosphonic acid methyl ester, phosphonic acid phenyl ester, phosphinic acid tert-butyl ester, methylphosphinic acid phenyl ester, benzenephosphinic acid phenyl ester, and the like; and, metal salts of the foregoing such as sodium hypophosphite, calcium hypophosphite, zinc hypophosphite, aluminum hypophosphite, sodium phosphite, calcium phosphite, zinc phosphite, aluminum phosphite, ferric phosphite, sodium benzenephosphinate, sodium methylphosphinate, and the like.

In another embodiment of the invention, the reactant which generates alkene or cycloalkene in situ is represented by the general formula $$R^4—X \qquad (II)$$

wherein:
$R^4$ is alkyl of up to 30 carbon atoms or cycloalkyl of from 3 to 12 carbon atoms; and,
X is halogen,

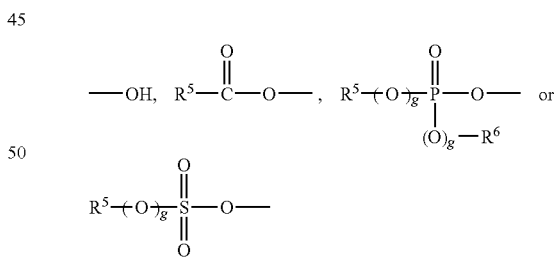

in which $R^5$ and $R^6$ each independently is H, alkyl of up to 30 carbon atoms, cycloalkyl of from 3 to 12 carbon atoms or aryl of from 6 to 20 carbon atoms and g is 0 or 1.

In reactant (II), $R^4$ is preferably branched alkyl since branching more readily provides alkene alkylating agent.

Illustrative of useful halides $R^4$—X are 2-chloro-2-methylpropane, 2-bromo-2-methylpropane, 2-chloropropane, 2-bromopropane, tert-amyl chloride, tert-amyl bromide, and the like.

Useful alcohols of structure $R^4$—OH include tert-butyl alcohol, tert-amyl alcohol, isopropyl alcohol, 2-butanol, 2-buten-1-ol and 2-methyl-3-buten-2-ol. Likewise suitable are cyclic alcohols, in particular, 1-methylcyclopentanol, 1-methycycloheptanol, 1-methylcyclooctanol and 1-methylcyclodecanol.

Useful esters of the structures

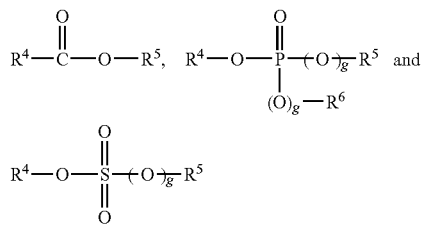

include tert-butyl acetate, phosphoric acid tert-butyl ester, phosphonic acid tert-butyl ester, phosphonic acid di-tert-butyl ester, diisobutylphosphinic acid tert-butyl ester, isopropyl tosylate, isopropyl mesylate, and the like.

As free-radical initiators, advantageous use is made of azo compounds. Preferably, the azo compounds are cationic and/or non-cationic azo compounds. Preferably, as cationic azo compounds, use is made of 2,2'-azobis(2-amidinopropane) dihydrochloride or 2,2'-azobis(N,N-dimethyleneisobutyramidine) dihydrochloride. Preferably, as non-cationic azo compounds, use is made of azobis(isobutyronitrile) (AIBN), 4,4'-azobis(4-cyanopentanoic acid) or 2,2'-azobis(2-methylbutyronitrile).

Preferably, as free-radical initiators, use is also made of inorganic peroxide and/or organic peroxide free-radical initiators.

Preferably, as inorganic peroxide free-radical initiators, use is made of hydrogen peroxide, ammonium peroxodisulfate and/or potassium peroxodisulfate.

Preferably, as organic peroxide free-radical initiators, use is made of dibenzoyl peroxide, di-tert-butyl peroxide, tert-butyl peroxybenzoate and/or peracetic acid.

Preferably, UV light initiation alone or in combination with above-mentioned initiators is employed.

Preferably, the reaction is carried out in the presence of carboxylic or mineral acid. Particularly preferably, the carboxylic acid is acetic acid and the mineral acid is sulfuric acid.

Preferably, the reaction is carried out at a temperature of from about 25 to about 130° C. Particularly preferably, the reaction is carried out at a temperature of from about 60° C. to about 120° C. Preferably, the reaction is carried out at atmospheric pressure. If generated in situ, an alkene tends to evaporate from the reaction vessel prior to reacting with P—H in which case a condenser can be used in order to return the alkene to the reaction vessel. Alternatively, a pressure of about 1-2 atmospheres can be applied in order to prevent evaporation of the alkene.

The present invention also relates in particular to a process in which hypophosphorous acid or sodium hypophosphite is reacted with tert-butyl alcohol or tert-butyl acetate in the presence of azo free-radical initiator or in the presence of a peroxide free-radical initiator to give diisobutyl phosphinic acid and/or sodium salt thereof as main product.

The invention also relates to the use of the dialkyphosphinic acids and/or alkali metal salts thereof obtained by the above-described process for preparing salts of such metals as Mg, Ca, Al, Zn, Fe(II), Fe(III), Cu(II), Zr(IV). These salts find use as flame retardants for thermoplastic polymers such as poly(ethylene terephthalate), polybutylene terephthalate), polystyrene, polyamide, polyethylene, polypropylene, and the like, and thermoset resins such as epoxy, phenolic or bismaleimide resins, and the like. The dialkylphosphinic acids and/or alkali metal salts thereof obtained by the above-described process are also used as intermediates in the pharmaceutical industry.

The process of the invention is illustrated by the examples which follow.

Example 1

Into a 250 ml three-necked flask equipped with condenser, addition funnel, magnetic stirrer and thermometer were charged 47.79 g (0.362 mol) 50% commercial hypophosphorous acid, 45.94 g (0.395 mol) tert-butyl acetate and 3.2 g AIBN. The reaction mixture was heated to 61° C. and stirred for 3 hours. Thereafter, a second portion of 8.7 g AIBN in acetic acid solution was gradually added while the temperature of the reaction mixture was slowly raised to 84° C. over the course of 11 hours. After addition was complete, $^{31}$P NMR analysis indicated the formation of 8% di-isobutylphosphinic acid, 63% isobutylphosphinic and 29% hypophosphorus acid. The reaction mixture was either neutralized by aqueous sodium hydroxide solution and then treated with aqueous aluminum hydroxide or directly reacted with aluminum oxide. The resulting white precipitate was filtered out, washed with water and dried in an oven thus providing 23 g aluminum salt of isobutylphosphinic acid. The mother liquor can, if desired, be recycled and used for preparing another quantity of product.

Example 2

Into a 500 ml three-necked flask equipped with condenser, addition funnel, magnetic stirrer and thermometer were charged 65.80 g (0.498 mol) 50% commercial hypophosphorous acid and 79.92 g (1.08 mol) tert-butyl alcohol. The reaction mixture was heated to 70° C. and addition of 2.06 g AIBN in 35 g acetic acid solution begun. After 6 hours, the addition was complete. The mixture contained 50% isobutylphosphinic acid and 50% hypophosphorus acid as determined by $^{31}$P NMR. The mixture was treated with a second portion of 5.5 g AIBN and 5.7 g t-butyl peroxybenzoate in acetic acid while the temperature was gradually increased to 97° C. over the course of 10 hours. After addition was complete, the mixture was found to contain 75% di-isobutylphosphinic acid, 20% isobutylphosphinic acid and 5% isobutylphosphonic acid. The mixture was dried in a rotavapor under vacuum at 75° C. to remove water and solvent and washed with warm water three times. The upper oily phase was separated and dried in a rotavapor under vacuum at 75° C. 57.5 g. The oily material was collected and crystallized at room temperature. The yield based on hypophosphorous acid was 65% without recycling the mother liquid. The mother liquid can, if desired, be recycled and used for preparing another quantity of product.

Example 3

Into a 2 L four-necked flask equipped with condenser, addition funnel, mechanical stirrer and thermometer were charged 321.35 g (3.03 mol) sodium hypophosphite monohydrate and 637 g acetic acid. After the solution became clear, 149.33 g sulfuric acid was gradually added to the mixture and a slurry was observed. A solution comprised of 458.18 g (6.186 mol) tert-butanol, 107.85 g acetic acid and 18.63 g (0.13 mol) di-tert-butyl peroxide was slowly added at a temperature of from 104 to 110° C. over 14.5 hours. Analysis of the mixture by $^{31}$P NMR showed it to contain 58 mol % diisobutylphosphinic acid and 42 mol % monoisobutylphosphinic acid. There was no measurable amount of hypophosphorus acid as determined by $^{31}$P NMR analysis. A portion of the solvent was then removed. Another solution comprising 98.80 g (1.33 mol) tert-butanol, 5.87 g (0.040 mol) di-tert-butyl peroxide and 23.7 g acetic acid was added to the reaction mixture at a temperature of from 103 to 111° C. over 7 hours. $^{31}$P NMR analysis indicated a mixture of 73% diisobutylphosphinic acid and 25% monoisobutylphosphinic acid with the remainder made up of monoisobutylphosphonate acid and phosphorus acid.

Example 4

The alkylated product mixture obtained in Example 3, supra, was filtered and the solvents were stripped out in a rotavapor under vacuum. The liquid mixture was then consecutively washed with 200 mL water, 200 mL 2.7% sodium carbonate three times and 200 mL water twice. The upper layer was separated and dried in a Rotavapor under vacuum. The material crystallized upon standing at room temperature to provide 350 g pure diisobutylphosphinic acid. The yield was 65%.

Example 5

A portion of the above pure diisobutylphosphinic acid (135.01 g, 0.758 mol) was mixed with water and neutralized with dilute aqueous sodium hydroxide solution. The neutralized product was then mixed with a solution of 61.83 g (0.256 mol) AlCl$_3$ 6H$_2$O in 2 L water. A large amount of white precipitate was observed. The precipitate was filtered and dried to a constant weight in an oven at 105° C. A white powder, aluminum salt of diisobutylphosphinic acid, of 139.43 g was obtained. The yield was 98.9%.

Example 6

Into a 1 L four-necked flask equipped with condenser, addition funnel, mechanical stirrer and thermometer were charged 187.52 g (1.77 mol) sodium hypophosphite monohydrate and 294 g acetic acid. After the solution became clear, 88.18 g sulfuric acid was gradually added thereto and a slurry was observed. A solution comprised of 150.81 g (2.03 mol) tert-butanol, 16.97 g acetic acid and 6.35 g (0.043 mol) di-tert-butyl peroxide was slowly added at a temperature range of from 111 to 118° C. over 6 hours. Analysis of the mixture by $^{31}$P NMR showed the mixture to consist of 13 mol % diisobutylphosphinic acid, 72 mol % monoisobutylphosphinic acid and 13% hyposphosphorus acid. Another solution comprising 156.577 g (2.11 mol) tert-butanol, 11.86 g di-tert-butyl peroxide (0.081 mol) and 160.29 g acetic anhydride was then added to the reaction mixture at a temperature of 104 to 111° C. over 14.5 hours while 13.71 g sulfuric acid was added from a second funnel. A mixture of 87.5% diisobutylphosphinic acid, 9.5% monoisobutylphosphinic acid, 1.6% monoisobutylphosphonic acid and 1.4% phosphorus acid was obtained.

Example 7

The alkylated product mixture obtained in Example 6, supra, was first filtered and then stripped in a Rotavapor at a bath temperature of 100° C. A solution of 302 g was obtained. Part of this solution (233 g, total 1.37 mol P) was neutralized with diluted sodium hydroxide and added to 2.5 L 4% aqueous aluminum chloride (0.435 mol AlCl$_3$ 6H$_2$O). The resulting white precipitate was filtered and dried in an oven at 75° C. overnight. 214 g of white powder, aluminum salts of diisobutylphinic acid, monoisobutylphosphinic acid and monoisobutylphosphonic acid, was obtained.

Example 8

Into a 2 L four-necked flask equipped with condenser, addition funnel, mechanical stirrer and thermometer were charged 211.76 g (2.00 mol) sodium hypophosphite monohydrate and 317 g acetic acid. After the solution became clear, 106.97 g sulfuric acid was gradually added to the mixture and a slurry was observed. The mixture was then heated to 120° C. A solution comprised of 243.19 g (2.09 mol) tert-butyl acetate and 7.35 g (0.050 mol) di-tert-butyl peroxide was slowly added at a temperature of 115 to 120° C. over 5 hours. Analysis of the mixture by $^{31}$P NMR showed the mixture contained 11 mol % diisobutylphosphinic acid, 72 mol % monoisobutylphosphinic acid and 17 mol % hypophosphorus acid. A further 20.12 g sulfuric acid was added. Another solution comprising 310.73 g (2.68 mol) tert-butyl acetate and 13.10 g (0.090 mol) di-tert-butyl peroxide was added to the reaction mixture at a temperature of 114 to 120° C. over 10 hours. $^{31}$P NMR analysis indicated the mixture to contain 88% diisobutylphosphinic acid and 10% monoisobutylphosphinic acid with the remainder made up of monoisobutylphosphonate acid and phosphorus acid.

Example 9

The alkylated product mixture obtained in Example 8, supra, was filtered and the solvents were stripped out in a rotavapor under vacuum. The liquid was mixed with 100 mL toluene and consecutively washed by 200 mL water, 150 mL 3.8% sodium carbonate three times and 100 mL water twice respectively. The upper layer was separated and dried at a Rotavapor under vacuum. The layer crystallized upon standing at room temperature to provide 288 g pure diisobutylphosphinic acid. The yield was 81%.

While the process of the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out the process of the invention but that the invention will include all embodiments falling within the scope of the appended claims.

What is claimed is:

1. A process for alkylating a phosphorus-containing compound to provide an alkylated phosphorus-containing compound which comprises alkylating phosphorus-containing compound possessing at least one phosphorus-hydrogen

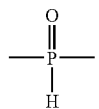

alkylatable site with reactant which generates alkene and/or cycloalkene alkylating agent in situ in the presence of initiator, the alkylene and/or cycloalkylene alkylating agent alkylating the phosphorus-containing component to provide alkylated phosphorus-containing product wherein phosphorus-containing compound is represented by general formula (I):

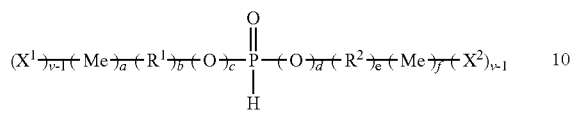
(I)

wherein:

$X^1$, where present, is

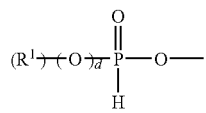

and $x^2$, where present, is

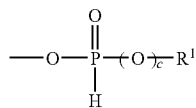

in which $R^1$ is H, alkyl of up to 30 carbon atoms, cycloalkyl of from 3 to 12 carbon atoms or aryl of from 6 to 20 carbon atoms; Me is a metal having a valence v of 1, 2, 3 or 4; $R^2$ is H, alkyl of up to 30 carbon atoms, cycloalkyl of from 3 to 12 carbon atoms or aryl of from 6 to 20 carbon atoms; and, a, b, c, d, e and f each independently is 0 or 1, provided, when a=1, c=1 and b=0, when b=1, a=0 and $x^1$ is not present, when f=1, d=1 and e=0, and when e=1, f=0 and $x^2$ is not present, and the reactant which generates alkene or cycloalkene in situ is represented by general formula (II):

$R^4$—X  (II)

wherein:

$R^4$ is alkyl of up to 30 carbon atoms or cycloalkyl of from 3 to 12 carbon atoms; and, X is 

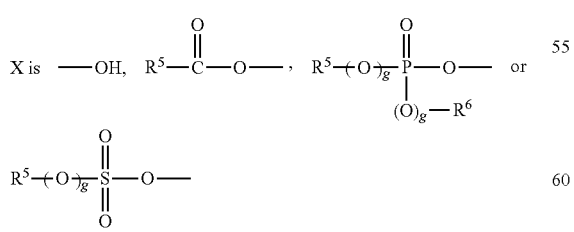

in which $R^5$ and $R^6$ each independently is H, alkyl of up to 30 carbon atoms, cycloalkyl of from 3 to 12 carbon atoms or aryl of from 6 to 20 carbon atoms and g is 0 or 1.

2. The process of claim 1 wherein phosphorous-containing compound (I) is selected from the group (1)-(6) consisting of:

(1)

(2)

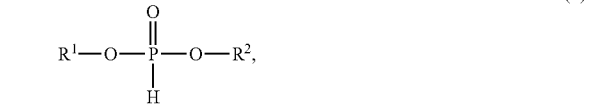
(3)

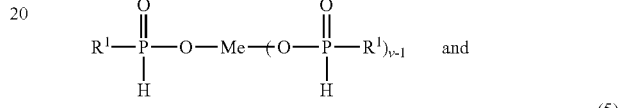
(4)

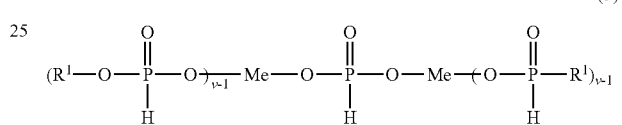
(5)

in which $R^1$, $R^2$, Me and v have the aforestated meanings.

3. The process of claim 2 wherein in phosphorus-containing compounds (1)-(6), $R^1$ is H and Me is lithium, sodium, potassium, magnesium, calcium, barium, aluminum, titanium, vanadium, chromium, molybdenum, iron, cobalt, nickel, copper or zinc.

4. The process of claim 3 wherein in phosphorus-containing compounds (2) and (3), $R^2$ is H.

5. The process of claim 1 wherein phosphorus-containing compound (I) is at least one member selected from the group (1)-(6) consisting of:

(1)

(2)

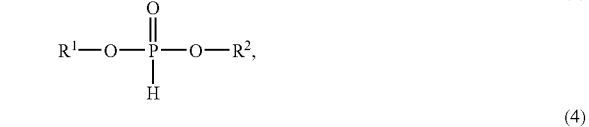
(3)

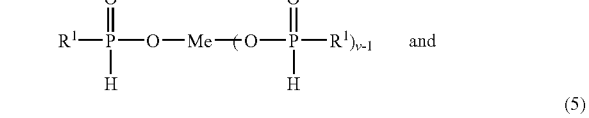
(4)

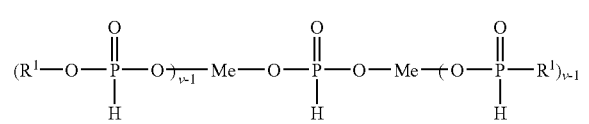
(5)

in which $R^1$, $R^2$, Me and v have the aforestated meanings.

6. The process of claim 5 wherein in phosphorus-containing compounds (1)-(6), $R^1$ is H and Me is lithium, sodium, potassium, magnesium, calcium, barium, aluminum, titanium, vanadium, chromium, molybdenum, iron, cobalt, nickel, copper or zinc.

7. The process of claim 6 wherein in phosphorus-containing compounds (2) and (3), $R^2$ is H.

8. The process of claim 1 wherein the phosphorus-containing compound is at least one member of the group consisting of phosphonic acid, hypophosphorous acid, phosphinic acid, phosphinous acid, phosphonic acid tert-butyl ester, phosphonic acid di-tert-butyl ester, phosphonic acid methyl ester, phosphonic acid phenyl ester, phosphinic acid tert-butyl ester, methylphosphinic acid phenyl ester, benzenephosphinic acid phenyl ester, sodium hypophosphite, calcium hypophosphite, zinc hyposphosphite, aluminum hypophosphite, sodium phosphite, calcium phosphite, zinc phosphite, aluminum phosphite, ferric phosphite, sodium benzenephosphinate and sodium methylphosphinate.

9. The process of claim 1 wherein the reactant which generates alkene or cycloalkene in situ is at least one member of the group consisting of tert-butyl alcohol, tert-amyl alcohol, isopropyl alcohol, 2-butanol, 2-buten-1-ol, 2-methyl-3-buten-2-ol, 1-methylcyclopentanol, 1-methycycloheptanol, 1-methylcyclooctanol, 1-methylcyclodecanol, tert-butyl acetate, phosphoric acid tert-butyl ester, phosphonic acid tert-butyl ester, phosphonic acid di-tert-butyl ester, diisobutylphosphinic acid tert-butyl ester, isopropyl tosylate and isopropyl mesylate.

10. The process of claim 8 wherein the reactant which generates alkene or cycloalkene in situ is at least one member of the group consisting of tert-butyl alcohol, tert-amyl alcohol, isopropyl alcohol, 2-butanol, 2-buten-1-ol, 2-methyl-3-buten-2-ol, 1-methylcyclopentanol, 1-methycycloheptanol, 1-methylcyclooctanol, 1-methylcyclodecanol, tert-butyl acetate, phosphoric acid tert-butyl ester, phosphonic acid tert-butyl ester, phosphonic acid di-tert-butyl ester, diisobutylphosphinic acid tert-butyl ester, isopropyl tosylate and isopropyl mesylate.

11. The process of claim 1 wherein the initiator is at least one free radical initiator, UV light or a combination thereof.

12. The process of claim 11 wherein the free radical initiator is at least one azo compound, inorganic peroxide and/or organic peroxide.

13. The process of claim 11 wherein the free radical initiator is at least one member selected from the group consisting of 2,2'-azobis(2-amidinopropane) dihydrochloride, 2,2'-azobis(N,N'-dimethyleneisobutyramidine) dihydrochloride, azobis(isobutyronitrile), 4,4'-azobis(4-cyanopentanoic acid), 2,2'-azobis(2-methylbutyronitrile), hydrogen peroxide, ammonium peroxodisulfate, potassium peroxodisulfate, dibenzoyl peroxide, di-tert-butyl peroxide and peracetic acid.

14. The process of claim 1 carried out in the presence of carboxylic acid and/or mineral acid.

15. The process of claim 1 wherein the alkylation reaction is carried out at a temperature of from about 25° C. to about 130° C. and a pressure ranging from about atmospheric up to about 2 atmospheres.

16. The process of claim 5 wherein phosphorus-containing compound (I) is at least one member selected from the group consisting of (2) and (3), the alkylated reaction product thereafter being converted to the corresponding metal salt.

17. The process of claim 16 wherein the metal of said metal salt is selected from the group consisting of Mg, Al, Zn, Fe(II), Fe(III), Cu(II) and Zr(IV).

18. The process of claim 1 wherein:
the phosphorus-containing compound is at least one member of the group consisting of phosphonic acid, hypophosphorous acid, phosphinic acid, phosphinous acid, phosphonic acid tert-butyl ester, phosphonic acid di-tert-butyl ester;
phosphonic acid methyl ester, phosphonic acid phenyl ester, phosphinic acid tert-butyl ester, methylphosphinic acid phenyl ester, benzenephosphinic acid phenyl ester, sodium hypophosphite, calcium hypophosphite, zinc hyposphosphite, aluminum hypophosphite, sodium phosphite, calcium phosphite, zinc phosphite, aluminum phosphite, ferric phosphite, sodium benzenephosphinate and sodium methylphosphinate, the reactant which generates alkene or cycloalkene in situ is at least one member of the group consisting of tert-butyl alcohol, tert-amyl alcohol, isopropyl alcohol, 2-butanol, 2-buten-1-ol, 2-methyl-3-buten-2-ol, 1-methylcyclopentanol, 1-methycycloheptanol, 1-methylcyclooctanol, 1-methylcyclodecanol, tert-butyl acetate, phosphoric acid tert-butyl ester, phosphonic acid tert-butyl ester, phosphonic acid di-tert-butyl ester, diisobutylphosphinic acid tert-butyl ester, isopropyl tosylate and isopropyl mesylate; and,
the initiator is at least one free radical initiator, UV light or a combination thereof.

* * * * *